United States Patent [19]

Flower

[11] Patent Number: 5,688,231
[45] Date of Patent: Nov. 18, 1997

[54] IONTOPHORESIS ASSEMBLY INCLUDING CLEANABLE ELECTRICAL CONTACTS

[75] Inventor: Ronald J. Flower, Vernon, N.J.

[73] Assignee: Becton Dickinson and Company, Franklin Lakes, N.J.

[21] Appl. No.: 315,533

[22] Filed: Sep. 30, 1994

[51] Int. Cl.[6] ..................................................... A61N 1/30
[52] U.S. Cl. ...................................... 604/20; 439/387
[58] Field of Search ........................ 604/20–21; 607/152; 439/387, 909, 67, 260, 495, 725, 267

[56] References Cited

U.S. PATENT DOCUMENTS

| | | |
|---|---|---|
| 758,478 | 4/1904 | Rusby . |
| 1,808,555 | 6/1931 | Ishimaru . |
| 2,000,909 | 5/1935 | Alsaker . |
| 2,882,508 | 4/1959 | Watts . |
| 3,250,884 | 5/1966 | Larkin . |
| 3,590,198 | 6/1971 | Fischer . |
| 4,286,311 | 8/1981 | Maglica . |
| 4,472,614 | 9/1984 | Newland . |
| 4,647,140 | 3/1987 | Crawford ............................. 439/387 |
| 5,160,316 | 11/1992 | Henley ........................................ 604/20 |
| 5,224,928 | 7/1993 | Sibalis et al. ............................. 607/152 |
| 5,344,394 | 9/1994 | Gyory et al. ................................ 604/20 |

FOREIGN PATENT DOCUMENTS 652135B  6/1991  Australia ................... 604/20

OTHER PUBLICATIONS

IBM–Technical Disclosure Bulletin vol. 27, No. 12 May 1985. "Resilient Connector for Pluggable Module".

*Primary Examiner*—Mark Bockelman
*Attorney, Agent, or Firm*—Allen W. Wark

[57] ABSTRACT

An iontophoretic delivery system permits transcutaneous delivery of a drug contained on a patch. The system includes a flexible planar patch having a medicament-containing surface in contact with the skin of a patient. A controller supplies electrical current to effect iontophoretic delivery. Electrical connection is established between the controller and the patch. The connection is maintained free of contaminants which could adversely affect the electrical connection by employing an abrasive wiping surface to clean the electrical interconnection.

19 Claims, 4 Drawing Sheets

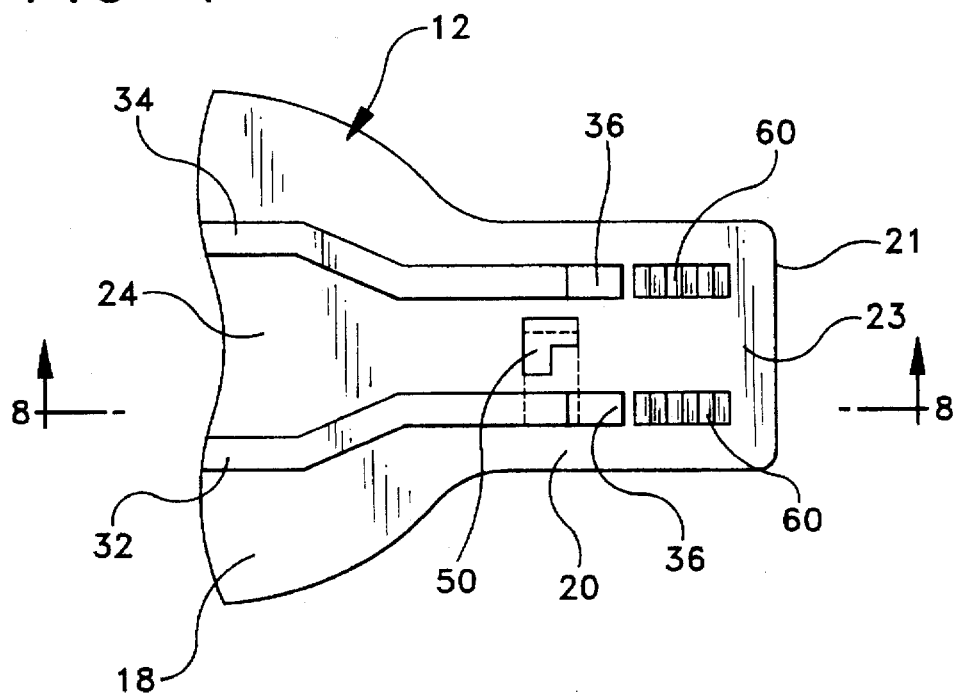
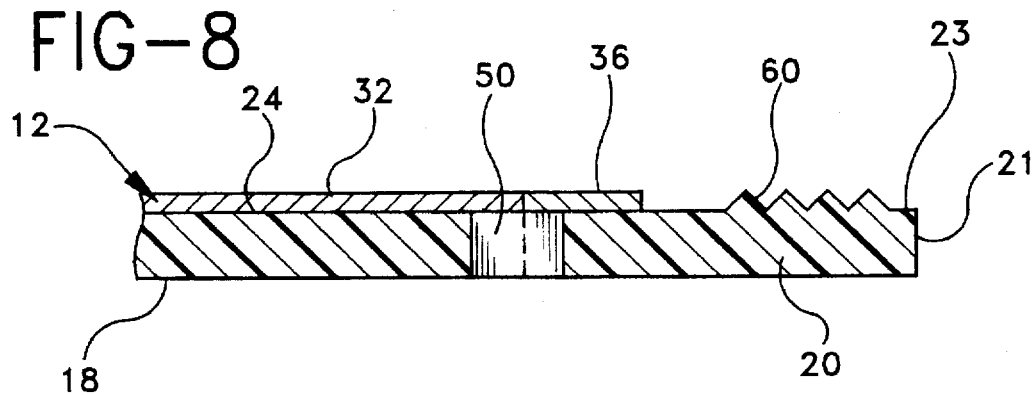
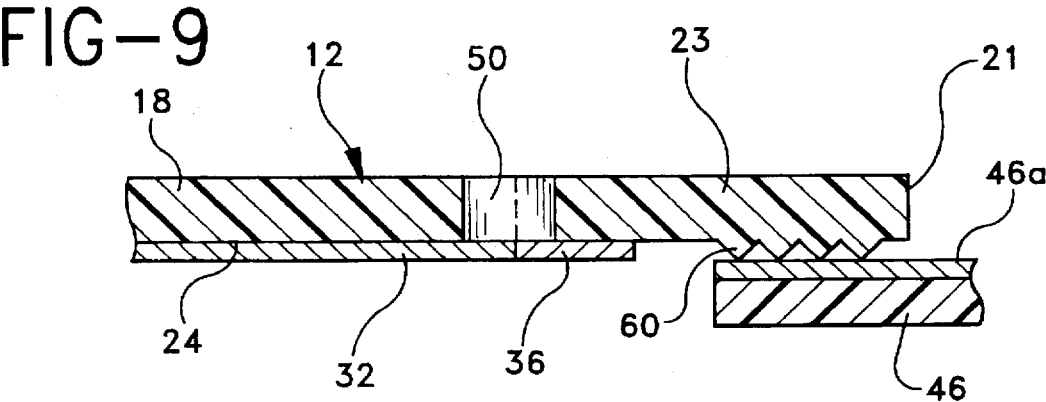

5,688,231

IONTOPHORESIS ASSEMBLY INCLUDING CLEANABLE ELECTRICAL CONTACTS

FIELD OF THE INVENTION

The present invention relates generally to an iontophoresis device for transcutaneous drug delivery. More particularly, the present invention relates to a drug-containing patch and a controller which establishes effective electrical connection therebetween to effect iontophoretic drug delivery.

BACKGROUND OF THE INVENTION

Iontophoresis has come into increasing attention as an effective method for the application of drugs through the skin.

In practice, the process of iontophoretic drug delivery is typically achieved by placing an ionic drug either in solution or in gel form on a carrier and placing the drug-containing carrier into contact with the skin. A pair of electrodes is placed in contact with the skin and with the carrier. Direct current is applied between the two electrodes. Under the influence of the electric field present, drug molecules migrate through the skin. As current flows between the two electrodes placed at spaced apart locations on the skin, the current path carries the drug with it.

The iontophoretic delivery system may include a disposable drug containing carrier such as an adhesive patch and a controller including a source of electrical power. The controller is connectable to the patch for providing the necessary current to deliver the drug. The patch is typically a flexible member which in addition to supporting the drug, also supports the electrodes which provide for iontophoretic delivery. The electrodes may be connected to the source of electrical current via electrical traces and pads on the patch. The controller may include the source of electrical power such as a battery and electrical contacts for interconnection with the pads of the patch.

Proper iontophoretic delivery of the drug contained on the patch through the skin of the patient is dependent upon the level and duration of the current applied across the electrodes. It is desirable that a good clean electrical signal be impressed across the electrodes so that proper administration of the drug is achieved. Further, as electrical current is being passed directly through the skin of the patient, fluctuations in current applied between the electrodes may be felt by the patient. It is not uncommon for the patient to experience slight discomfort if the current applied across the electrodes spikes or otherwise fluctuates. Such spikes or fluctuations can be caused by interference at the electrical interface between the patch and the controller. Dirt, debris or other contaminants lodged between the interconnecting surfaces may have a tendency to create electrical "noise" which can result in current variations.

It is well known to construct mating electrical contacts of the conductive spring variety where the contacts are interconnected with such force that the mating deflectable spring portions wipe against each other thereby cleaning the interconnection. However, as may be appreciated, in an iontophoretic delivery system the electrical pads of the patch are formed on a thin flexible surface which is unable to withstand the forces normally seen in mating spring contacts. This is because the patch is designed for single use. Such forces may have a tendency to scrape away the conductive pads or otherwise damage the conductive portions of the patch. An attempt to reduce the interconnection force may result in losing the benefit achievable by sliding spring-deflectable contacts against one another.

It is therefore desirable to provide an interconnection assembly which permits the reliable, clean interconnection between a drug-containing flexible patch, postionable on the skin of a patient, and a source of electrical current for permitting iontophoretic delivery of the drug.

SUMMARY OF THE INVENTION

It is an object of the present invention to provide an improved iontophoretic drug delivery system which is attachable to the skin of a patient for delivering a drug transcutaneously.

It is a further object of the present invention to provide an improved interconnectable iontophoretic drug delivery system including a medicament-containing patch and a controller where the controller provides electrical current for effecting iontophoretic delivery.

It is still a further object of the present invention to provide improved electrical connection between conductive portions of a medicament-containing flexible patch and electrical contacts of a controller.

In the efficient attainment of these and other objects, the present invention provides a disposable flexible medicament-containing patch and a controller for providing electrical current to the patch for iontophoretic drug delivery. The combination includes a flexible patch body having a medicament-containing portion and an insertion portion have a thin conductive pad thereon. A controller housing supports electronic components for generating electrical current and for insertably accommodating the insertion portion of the patch body. The controller housing includes an electrical contact for electrical connection with the conductive pad of the insertion portion of the patch body. One of the conductive pad or the electrical contact includes an abrasive surface at a forward location for slidable engagement with the other of the conductive pad or electrical contact, whereby the slidable engagement wipes away debris, contaminants, and the like from the other pad so as to establish good electrical engagement between the conductive pad and the electrical contact.

As more particularly described by way of the preferred embodiments herein, the insertion portion of the patch body includes an elongate flexible tab extending from the patch body having a distal edge insertable into the controller housing. The tab includes the conductive pad thereof spaced proximally from the edge of the tab and an abrasive surface disposed between the conductive pad and the distal edge. The abrasive surface may include plural ridges extending from the tab adjacent the distal edge which wipe against the electrical contact of the controller so as to wipe away debris or contaminants therefrom, thereby establishing good electrical engagement therebetween.

DETAILED DESCRIPTION OF THE PREFERRED EMBODIMENT

Figure 1:
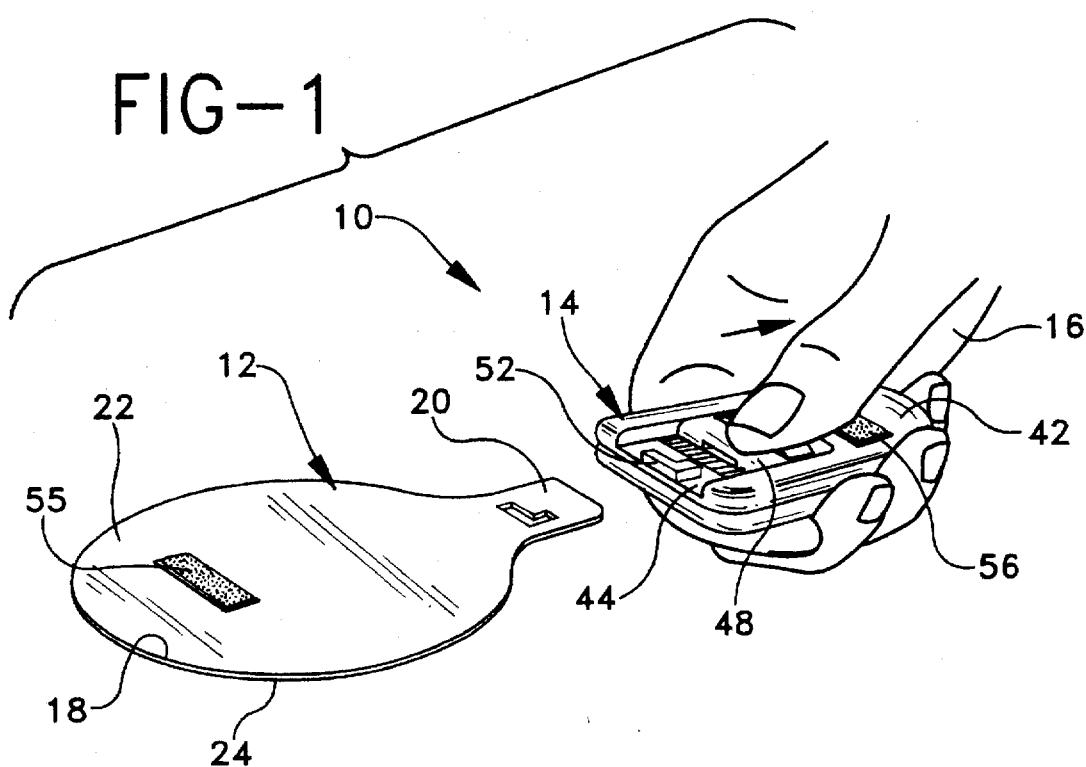
FIG. 1 is a perspective view of the combination of a patch and controller in accordance with the present invention.

Referring to FIG. 1, and iontophoretic patch and controller assembly 10 of the present invention is shown. Assembly 10 includes a patch 12 and a controller 14. Patch 12 is a generally planar flexible member formed of biocompatible material. Patch 12 may be formed of woven or non-woven textiles or polymers or may be any other construction well-known in the art. Patch 12 is typically adhesively supported on the skin of the patient. Patch 12 includes an enlarged patch body 18 and an extending narrow tab 20. Patch body 18 includes opposed planar surfaces 22 and 24. Planar surface 24 is disposed for skin contact and includes a drug reservoir 26 which contains an ionic drug typically in a gel form. While reservoir 26 is shown, any other technique known to place a drug in contact with the skin by use of a patch may also be employed. Skin contacting surface 24 further includes a pair of spaced apart electrodes 28 and 30. Each of electrodes 28 and 30 is positioned to be in contact with the skin upon placement of the patch 12 thereon. The positioning of electrodes 28 and 30 is such that an electrical current path is established between electrodes 28 and 30 through the skin of the patient. Electrode 28 is also placed in conductive contact with reservoir 26 in a manner well-known in the iontophoretic delivery art. A direct current source may be connected between the electrodes 28 and 30 such that electrode 28, in contact with reservoir 26, assumes the same charge as the ionized drug contained therein. Under the influence of electrical current passing from electrode 28 to electrode 30 through the skin, the drug contained in reservoir 26 is transcutaneously delivered.

Figure 2:
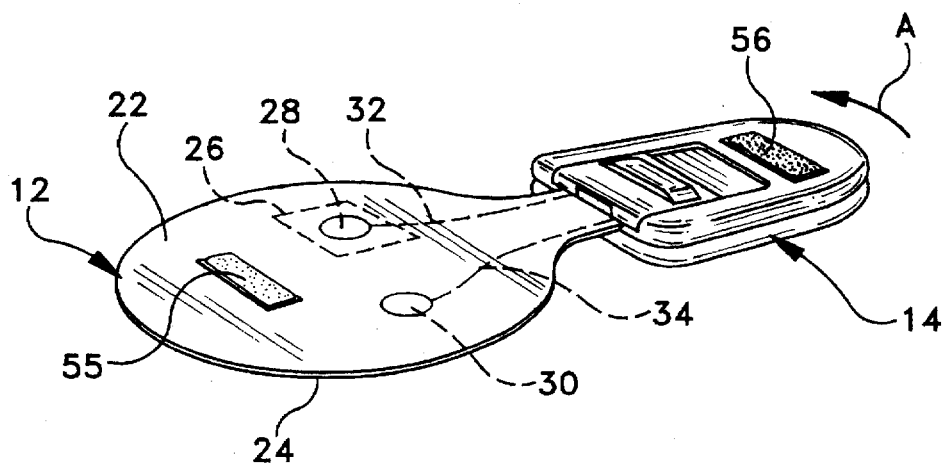
FIG. 2 is an enlarged plan view, partially broken away, of a tab portion of the patch shown in FIG. 1.

As further shown in FIG. 2, electrical current is supplied to electrodes 28 and 30 via electrical traces 32 and 34. Each of traces 32 and 34 may be one or more conductive paths extending from electrodes 28 and 30 to exposed conductive pads 36 positioned inwardly adjacent a marginal distal edge 31 of tab 20. Traces 32 and 34, as well as pads 36, may be formed by a deposition process which deposits a thin layer of conductive metal between electrodes 28, 30 and pads 36 on a flexible backing formed by surface 24 of patch 12. While suitably providing electrical continuity to electrodes 28 and 30, the traces 32 and 34 and pads 36 are relatively thin. As will be described in further detail hereinbelow, pads 36 are positioned for electrical connection to the source of electrical current.

Figure 4:
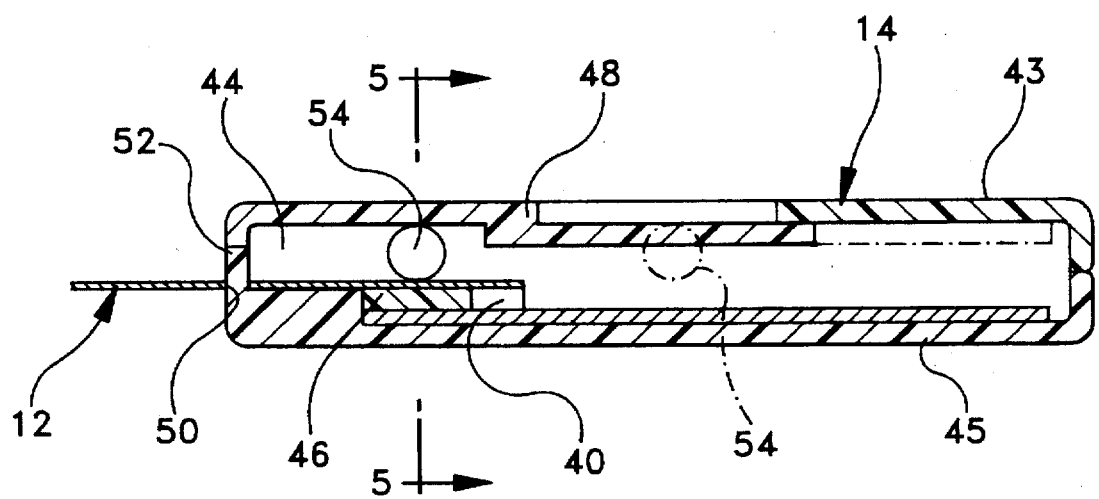
FIG. 4 is a sectional showing of the patch of FIG. 2 interconnected to the contacts of the controller housing.
Figure 5:
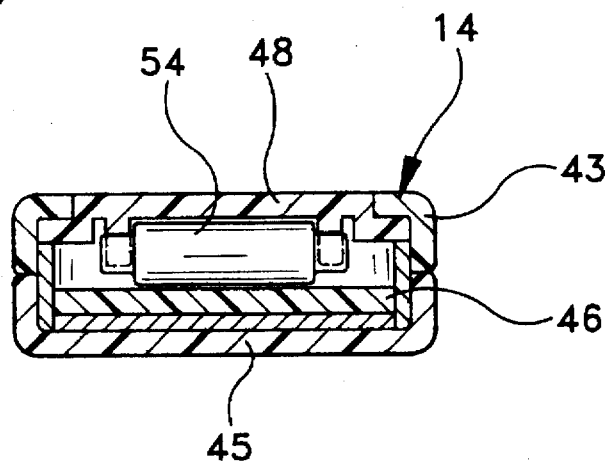
Figure 6:
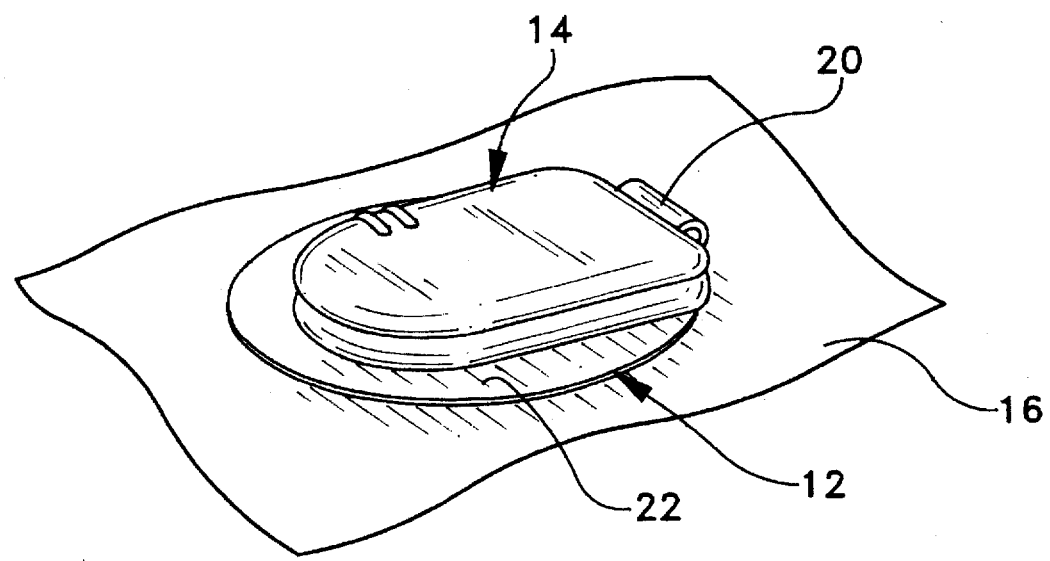

Referring additionally to FIG. 4, controller 14 houses electronic components 40 which supply the controlled application of electric current to electrodes 28 and 30. As is known in the art, electronic components 40 may include a source of electrical power such as a battery (not shown) and additional electronic components used to send a controlled electrical current to electrodes 28 and 30.

Figure 3:
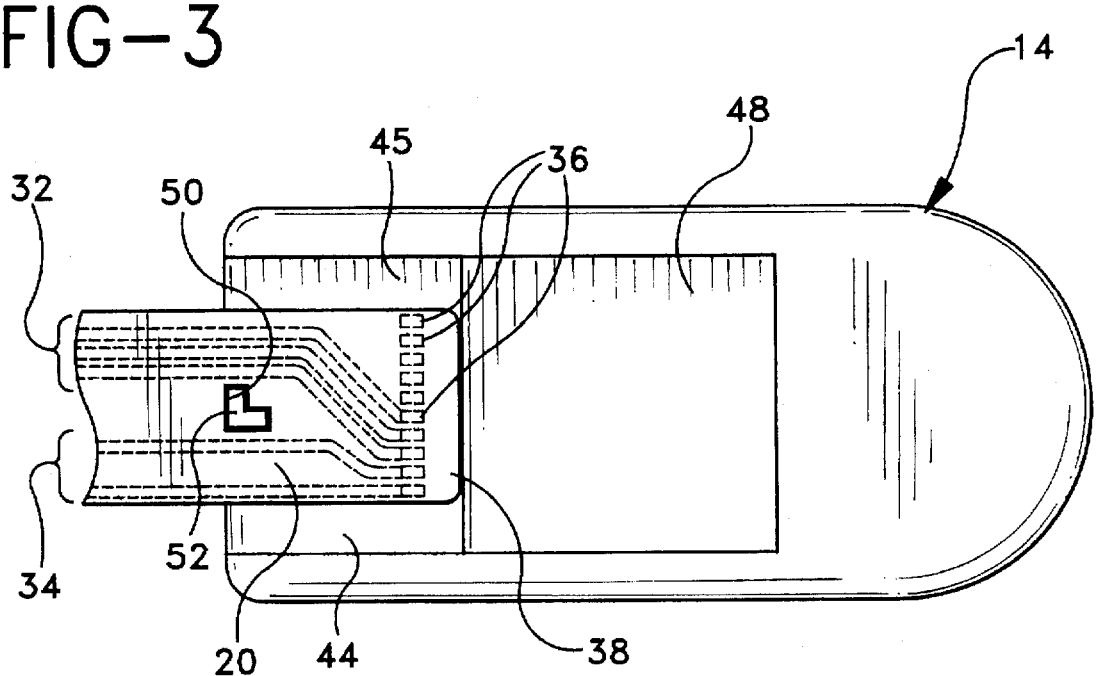
FIG. 3 is a sectional showing of a portion of the patch of FIG. 2 taken through the lines 3—3 thereof.

Referring to FIGS. 1 and 4, controller 14 may include a controller housing 42 which is generally rectangular in shape and includes a front end 44 which accommodates tab 20 of patch 12. Controller housing 42 may also support electrical spring contacts 46 (one of which being shown in FIGS. 3 and 4) extending from electronic components 40. Spring contacts 46 may be conventional electrical contacts formed of a suitably conductive metal and may include a resiliently deflectable, generally cantilevered portion 48 which extends towards tab 20 as shown in FIG. 4 for electrical interconnection with the conductive pads 36 thereon (FIG. 2). Contacts 46 are generally referred to as spring contacts as deflectability of cantilevered portions 48 provides sufficient spring force to provide intimate electrical engagement with a mating component. Conventional spring electrical contacts of this type are typically constructed to provide a mating insertion force between the cantilevered spring portion and a mating conductive surface, sufficient to provide a wiping engagement therebetween. The wiping engagement cleans the electrical interface of debris and other contaminants during interconnection. However, in the present invention as the conductive pads 36 of flexible tab 20 are extremely thin, such high degree of wiping force engagement could damage the conductive pads. Such force, if applied, may have a tendency to scrape away or otherwise damage the conductive pads. As shown in FIG. 3, the present invention provides for the ability to wipe clean the cantilevered portion 48 of contact 46 upon each connection and disconnection with patch 12 without exerting damaging force thereto.

Referring now to FIGS. 2–4, a portion of patch 12 is shown. Extending tab 20 which is designed for interconnection with controller 14 is generally elongate having a distal edge 21 which is insertable into the front end 44 of housing 42 (FIG. 4). Conductive pads 36 connected to traces 32 and 34 are preferably positioned at a location spaced proximally from distal edge 21 and are spaced transversely across tab 20. Tab 20 therefore includes a forward end extend 23 between pads 36 and distal edge 21 which is non-conductive. End extent 23 provides a leading portion which is initially insertable into controller housing 14. As end extent 23 is initially inserted into housing 14, it will engage cantilevered portion 48 of contact 46 prior to its engagement with pads 36. In that regard, end extent 23 may be formed to have an abrasive surface so as to wipe against the cantilevered portion 48 of contact 46.

The abrasive surface of end extent 23 may be formed by providing a plurality of ridges 60 which extend upwardly from tab 20. Ridges 60 may be formed integrally with the formation of patch 12 or may be applied or formed in a secondary operation. Ridges 60 are positioned adjacent each of conductive pads 36 so that prior to conductive engagement therewith, the resilient cantilevered portions 48 of contacts 46 slide against ridges 60, wiping any debris or contaminants therefrom. As patch 12 is initially inserted into controller housing 42, the resilient cantilvered portions 48 of contacts 46 slide along ridges 60, providing such wiping and cleaning. As shown in phantom in FIG. 3, further insertion provides for engagement between the now cleaned cantilevered portions 48 and pads 36. As may be appreciated, upon each occurrence of connection and disconnection of controller 14 and patch 12, the abrasive surface of end extent 23 will repeatedly wipe clean cantilevered portions 48. While ridges 60 are shown as the preferred manner for providing an abrasive surface to end extent 23 of tab 20, any other technique which would provide wiping engagement with cantilevered portions 48 of contacts 46 is also within the contemplation of the present invention.

As the wiping action is provided by the roughened or abrasive surface of the end extend 23 of tab 20, there is no need to construct the controller/patch assembly to apply a high degree of force between contacts 46 and pads 36 upon interconnection. This significantly reduces the opportunity to erode away or otherwise damage the thin conductive pads upon interconnection.

While tabs 20 are shown to have an abrasive surface adjacent the end thereof to wipe contacts 46 upon interconnection, it is further contemplated that with respect to controller 14, an abrasive surface may also be included on a forward portion of contacts 46 so as to wipe debris or contaminants from pads 36 prior to interconnection. However, this typically may not be necessary as the patch 12 may be provided in a clean sterile package for one time disposable use, while the controller is designed for multiple uses and thus may be more susceptible to contact corrosion.

Various changes to the foregoing described and shown structures would now be evident to those skilled in the art.

Accordingly, the particularly disclosed scope of the invention is set forth in the following claims.

What is claimed is:

1. In an iontophoresis drug delivery system, an assembly for providing electrical interconnection between a drug containing patch and an electrical controller, said assembly comprising:

electrical controller contacts mounted on the controller, said controller contacts receiving an electrical current from the controller;

electrical conductive pads positioned on the patch, said conductive pads being matable with said controller contacts to provide electrical interconnection between the controller and the patch; and abrasive wiping means affixed to the patch and positioned for wiping engagement with said controller contacts upon said interconnection, whereby said controller contacts are wiped clean of contaminants and debris immediately prior to said electrical interconnection.

2. An assembly of claim 1 wherein each said controller contact includes a deformable cantilvered spring contact portion for electrical engagement with patch contacts.

3. An assembly of claim 2 wherein said patch includes an insertion extent matable with said controller, said insertion extent supporting said patch contacts at a location spaced from an insertion edge thereof.

4. An assembly of claim 3 wherein said insertion extent of said patch includes said abrasive wiping means located between said insertion edge and said patch contacts for wiping engagement with said deformable cantilevered spring contact portion of said controller contact immediately before said electrical engagement of said cantilevered spring contact portions with said patch contacts.

5. An assembly of claim 4 wherein said insertion portion of said patch is generally a flexible member and wherein said abrasive wiping means includes raised ridges formed in said insertion extent between said insertion edge and said patch contacts.

6. An assembly of claim 5 wherein said patch contacts include conductive pads deposited on a surface of said insertion extent of said patch.

7. In combination, a disposable flexible patch containing medicament for iontophoretic delivery and a controller for providing electrical current to said patch for controlling said medicament delivery, said combination comprising:

a patch body having a medicament-containing portion and an insertion portion, said insertion portion having a thin electrically conductive pad thereon, said conductive pad being electrically connected to an electrode proximate said medicament containing portion;

a controller housing supporting electronic components for generating said electrical current, said controller housing having an opening for insertably accommodating said insertion portion of said patch body, said controller including an electrical contact supported by one of said controller housing and said electronic components, said contact being electrically coupled to said electronic components to receive said current therefrom, said contact providing electrical connection with said conductive pad of said patch body upon said insertable accommodation in said controller housing; and an abrasive surface, said abrasive surface positioned at a forward location of said insertion portion of said patch body for engagement with said electrical contact, whereby said engagement wipes away debris or contaminants so as to establish good electrical engagement between said conductive pad and said electrical contact.

8. A combination of claim 7 wherein said insertion portion of said patch body includes said abrasive surface.

9. A combination of claim 8 wherein said insertion portion of said patch body includes an elongate flexible tab extending from said patch body having a distal edge insertable into said controller housing, said tab having said conductive pad spaced proximally of said edge and wherein said abrasive surface is disposed between said conductive pad and said distal edge.

10. A combination of claim 9 wherein said abrasive surface includes plural ridges extending from said tab.

11. A combination of claim 10 wherein said electrical contact includes a deformable cantilevered spring portion for electrical engagement with said conductive pad.

12. A combination of claim 11 wherein said deformable cantilevered spring portion is engagable with said ridges extending from said tab immediately prior to said electrical engagement with said conductive pad.

13. A combination of claim 9 wherein said insertion portion of said patch body includes plural electrically isolated conductive pads transversely spaced across said tab and wherein said abrasive surface includes plural extending ridges adjacent each conductive pad of said insertion portion of said patch body.

14. A combination of claim 13 wherein said plural ridges are formed integrally with said patch body.

15. A combination of claim 13 wherein said ridges are non-conductive.

16. A disposable patch containing medicament for iontophoretic delivery when interfaced to a controller having at least one contact for providing electrical current to said patch for controlling said medicament delivery, said patch comprising:

a patch body having a medicament-containing portion and an insertion portion, said insertion portion having at least one thin electrically conductive pad thereon, said medicament-containing portion having at least one electrode thereon, said at least one conductive pad being electrically connected to said at least one electrode; and an abrasive surface, said abrasive surface positioned at a forward location of said insertion portion of said patch body for engagement with the at least one contact within the controller, whereby said engagement wipes away debris and contaminants so as to establish good electrical engagement between said at least one conductive pad and the at least one contact.

17. A disposable patch, as defined by claim 16, wherein said insertion portion of said patch body includes an elongate flexible tab extending from said patch body, said tab having a distal edge, said at least one conductive pad being disposed on said tab, and wherein said abrasive surface is disposed proximate said distal edge.

18. A disposable patch, as defined by claim 17, wherein said abrasive surface includes plural ridges, said ridges extending from said tab.

19. A disposable patch, as defined by claim 18, wherein said ridges are non-conductive.

* * * * *